(12) United States Patent
Rothenberg et al.

(10) Patent No.: US 6,725,859 B1
(45) Date of Patent: Apr. 27, 2004

(54) APPARATUS FOR DELIVERING AIR-BORNE SUBSTANCES

(75) Inventors: Simon J. Rothenberg, N. Wales, PA (US); Hsu Chi Yeh, Albuquerque, NM (US); Bernard J. Greenspan, San Diego, CA (US)

(73) Assignee: Charles River Laboratories, Wilmington, MA (US)

( * ) Notice: Subject to any disclaimer, the term of this patent is extended or adjusted under 35 U.S.C. 154(b) by 765 days.

(21) Appl. No.: 09/006,982

(22) Filed: Jan. 14, 1998

Related U.S. Application Data

(60) Provisional application No. 60/035,427, filed on Jan. 22, 1997.

(51) Int. Cl.[7] .............................................. A61M 11/00
(52) U.S. Cl. .............................. 128/200.23; 128/200.14
(58) Field of Search ........................ 128/200.14, 207.18, 128/200.23, 200.17, 204.18; 604/140; 424/438; 119/420

(56) References Cited

U.S. PATENT DOCUMENTS

| | | | | |
|---|---|---|---|---|
| 4,479,493 A | * | 10/1984 | Bung et al. ............. | 128/204.18 |
| 4,554,916 A | * | 11/1985 | Watt ....................... | 128/203.12 |
| 4,653,494 A | * | 3/1987 | Ruderian ............... | 128/203.22 |
| 4,694,824 A | * | 9/1987 | Ruderian ............... | 128/203.22 |
| 4,721,060 A | * | 1/1988 | Cannon et al. ......... | 128/204.18 |
| 4,723,958 A | | 2/1988 | Pope et al. .............. | 604/890.1 |
| 4,781,146 A | * | 11/1988 | Spengler ................ | 128/204.18 |
| 4,860,741 A | * | 8/1989 | Bernstein et al. ...... | 128/204.18 |
| 4,926,852 A | * | 5/1990 | Zoltan et al. .......... | 128/200.23 |
| 5,002,048 A | * | 3/1991 | Makiej, Jr. ............. | 128/200.23 |
| 5,007,419 A | * | 4/1991 | Weinstein et al. ..... | 128/200.23 |
| 5,099,792 A | * | 3/1992 | Cannon et al. ......... | 119/420 |
| 5,169,029 A | * | 12/1992 | Behar et al. ........... | 128/200.23 |
| 5,297,502 A | * | 3/1994 | Jaeger ................... | 128/204.18 |
| 5,391,381 A | | 2/1995 | Wong et al. ............ | 424/473 |
| 5,437,267 A | * | 8/1995 | Weinstein et al. ..... | 128/200.23 |
| 5,709,202 A | | 1/1998 | Lloyd et al. ........... | 128/200.14 |
| 5,896,829 A | * | 4/1999 | Rothenberg et al. ... | 119/420 |

FOREIGN PATENT DOCUMENTS

SU      1509083    *   9/1989      128/200.14

OTHER PUBLICATIONS

Merriam Webster's Collegiate 10th ed., Merriam–Webster, Inc. Dec. 1997.*

* cited by examiner

*Primary Examiner*—Weilun Lo
(74) *Attorney, Agent, or Firm*—Woodcock Washburn LLP

(57) ABSTRACT

Apparatus and methods for delivery of air-borne materials from pulsatile delivery devices by passing the emissions from such devices and air in a coaxial manner through a suitable mixing chamber. Preferred apparatus include a chamber defining an axis of air flow, a plurality of pulsatile delivery devices, an actuator in communication with the devices for selective actuation thereof, and a device for introducing air at a first end of the chamber and for flowing that air substantially along the axis. The pulsatile delivery devices are positioned at the first end of the chamber such that actuation of the devices emits an air-borne substance substantially along the axis of air flow.

27 Claims, 4 Drawing Sheets

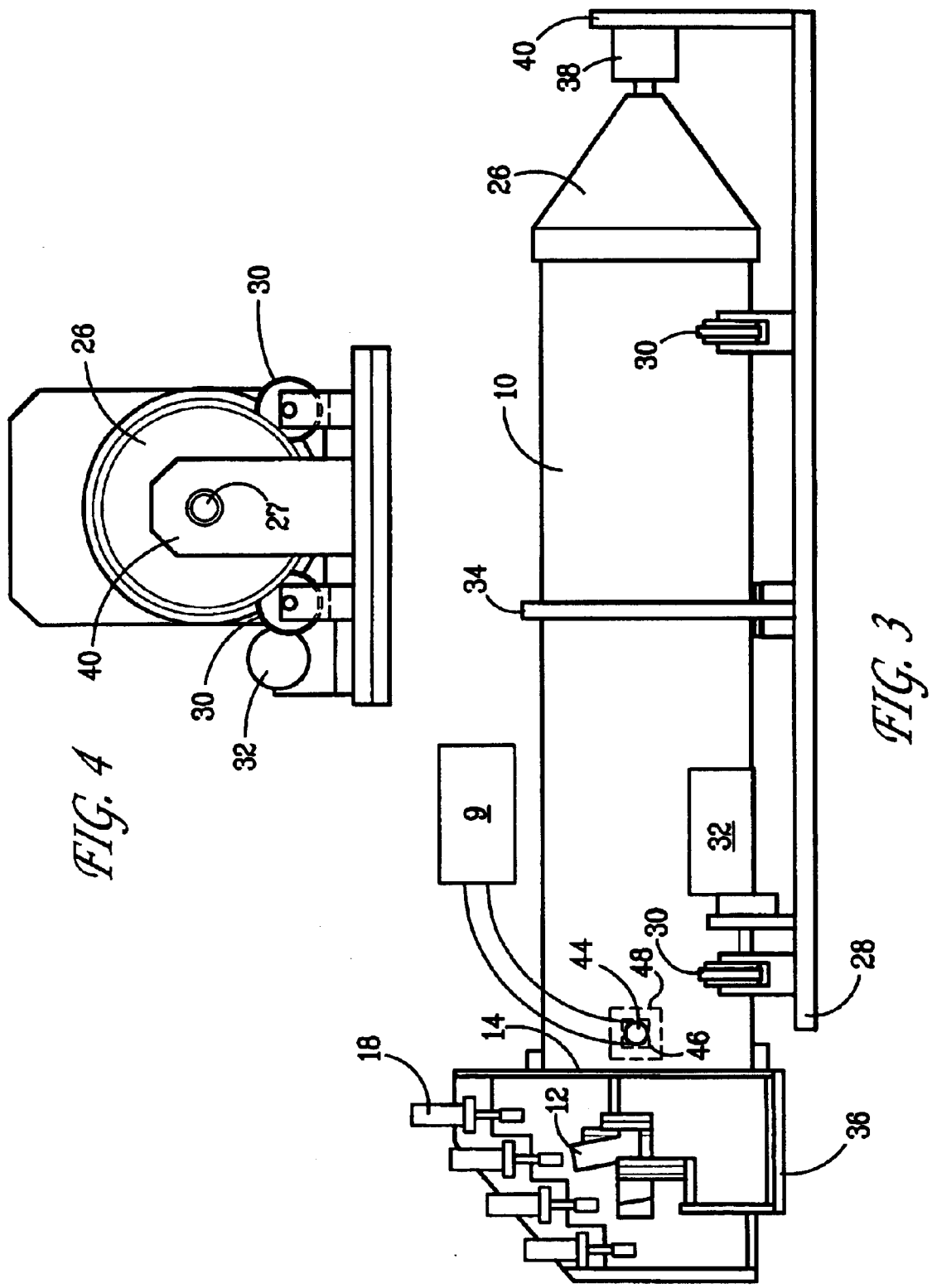

| Exposure Day | 4mg/kg/day 0.027mg/L Filter Weight | Conc. | 4mg/kg/day 0.027mg/L Filter Weight | Conc. | 30mg/kg/day 0.2mg/L Filter Weight | Conc. | 30mg/kg/day 0.2mg/L Filter Weight | Conc. | 60mg/kg/day 0.4mg/L Filter Weight | Conc. | 60mg/kg/day 0.4mg/L Filter Weight | Conc. | 120mg/kg/day 0.8mg/L Filter Weight | Conc. |
|---|---|---|---|---|---|---|---|---|---|---|---|---|---|---|
| 1 | 0.863 | 0.022 | 1.004 | 0.025 | 1.181 | 0.148 | 1.442 | 0.180 | 1.515 | 0.379 | 1.480 | 0.370 | 1.040 | 0.520 |
| 2 | 1.103 | 0.028 | 1.018 | 0.025 | 1.076 | 0.135 | 1.811 | 0.026 | 1.329 | 0.332 | 1.911 | 0.478 | 1.236 | 0.618 |
| 3 | 1.015 | 0.025 | 0.840 | 0.021 | 1.990 | 0.249 | 2.193 | 0.274 | 1.507 | 0.377 | 1.870 | 0.468 | 1.309 | 0.655 |
| 4 | 1.090 | 0.027 | 1.090 | 0.027 | 1.020 | 0.128 | 1.609 | 0.201 | 1.299 | 0.325 | 1.472 | 0.368 | 1.875 | 0.938 |
| 5 | 1.370 | 0.034 | 0.869 | 0.022 | 1.608 | 0.201 | 1.534 | 0.192 | 1.347 | 0.337 | 1.472 | 0.368 | 1.875 | 0.938 |
| 6 | 1.063 | 0.027 | 1.070 | 0.027 | 1.273 | 0.159 | 1.692 | 0.212 | 1.765 | 0.441 | 1.542 | 0.386 | 1.155 | 0.578 |
| 7 | 1.303 | 0.033 | 1.085 | 0.027 | 1.852 | 0.232 | 1.921 | 0.240 | 1.476 | 0.369 | 1.853 | 0.463 | 1.251 | 0.626 |
| 8 | 1.266 | 0.032 | 1.217 | 0.030 | 1.813 | 0.277 | 1.685 | 0.211 | 1.356 | 0.339 | 1.529 | 0.382 | 1.779 | 0.890 |
| 9 | 1.082 | 0.027 | 1.115 | 0.028 | 2.179 | 0.272 | 2.162 | 0.027 | 1.652 | 0.413 | 1.958 | 0.490 | 1.219 | 0.610 |
| 10 | 1.088 | 0.027 | 1.125 | 0.028 | 1.819 | 0.227 | 1.457 | 0.182 | 1.284 | 0.321 | 1.288 | 0.322 | 1.444 | 0.722 |
| 11 | 1.240 | 0.031 | 0.979 | 0.024 | 1.471 | 0.184 | 1.729 | 0.216 | 1.379 | 0.345 | 1.471 | 0.368 | 1.468 | 0.734 |
| 12 | 1.075 | 0.027 | 1.059 | 0.026 | 1.679 | 0.210 | 1.121 | 0.140 | 1.255 | 0.314 | 1.537 | 0.384 | 1.473 | 0.737 |
| 13 | 1.119 | 0.028 | 1.047 | 0.026 | 1.631 | 0.204 | 1.648 | 0.206 | 1.451 | 0.363 | 1.675 | 0.419 | 1.044 | 0.522 |
| 14 | 1.002 | 0.025 | 0.931 | 0.023 | 1.467 | 0.183 | 1.272 | 0.159 | 1.232 | 0.308 | 1.478 | 0.370 | 1.449 | 0.725 |
| MEAN | 1.120 | 0.0280 | 1.032 | 0.026 | 1.576 | 0.197 | 1.663 | 0.208 | 1.418 | 0.354 | 1.610 | 0.402 | 1.351 | 0.675 |
| STD | 0.133 | 0.003 | 0.102 | 0.003 | 0.348 | 0.043 | 0.302 | 0.038 | 0.154 | 0.039 | 0.207 | 0.052 | 0.250 | 0.125 |

FIG. 5

| Exposure Day | 4 mg/kg/day 0.027 mg/L | | 4 mg/kg/day 0.027 mg/L | | 30 mg/kg/day 0.2 mg/L | | 30 mg/kg/day 0.2 mg/L | | 40 mg/kg/day 0.4 mg/L | | 60 mg/kg/day 0.4 mg/L | | 120 mg/kg/day 0.8 mg/L | |
|---|---|---|---|---|---|---|---|---|---|---|---|---|---|---|
| | MMAD | $\sigma_g$ | MMAD | $\sigma_g$ | MMAD | $\sigma_g$ | MMAD | $\sigma_g$ | MMAD | $\sigma_g$ | MMAD | $\sigma_g$ | MMAD | $\sigma_g$ |
| 1 | — | — | — | — | — | — | — | — | 1.93 | 2.52 | 2.04 | — | — | — |
| 2 | — | — | — | — | 1.43 | 1.96 | — | — | — | — | — | — | 2.47 | 2.43 |
| 3 | 2.08 | 2.06 | — | — | — | — | 2.02 | 2.52 | — | — | — | — | — | — |
| 4 | — | — | 2.03 | 2.17 | — | — | — | — | — | — | — | — | — | — |
| 5 | — | — | 2.65 | 2.72 | — | — | — | — | 2.50 | 2.32 | — | — | — | — |
| 6 | — | — | — | — | 2.50 | 2.72 | — | — | — | — | — | — | — | — |
| 7 | 2.20 | 2.18 | — | — | — | — | — | — | — | — | — | — | 2.30 | 2.52 |
| 8 | — | — | 1.78 | 2.16 | — | — | — | — | — | — | — | — | — | — |
| 9 | — | — | — | — | — | — | — | — | 2.52 | 2.50 | 2.15 | 2.47 | — | — |
| 10 | — | — | — | — | 2.53 | 2.37 | 1.92 | 2.92 | — | — | — | — | — | — |
| 11 | 1.97 | 2.21 | — | — | — | — | — | — | — | — | — | — | 2.55 | 2.75 |
| 12 | — | — | 1.97 | 2.40 | — | — | — | — | — | — | 2.30 | 2.13 | — | — |
| 13 | — | — | — | — | 2.35 | 2.28 | 2.75 | 2.24 | — | — | — | — | — | — |
| 14 | — | — | — | — | — | — | — | — | — | — | — | — | — | — |
| MEAN | 2.08 | 2.15 | 2.11 | 2.36 | 2.20 | 2.33 | 2.23 | 2.56 | 2.32 | 2.45 | 2.16 | 2.30 | 2.44 | 2.57 |
| STD | 0.12 | 0.08 | 0.38 | 0.26 | 0.52 | 0.31 | 0.45 | 0.34 | 0.34 | 0.11 | 0.13 | 0.17 | 0.13 | 0.17 |

FIG. 6

APPARATUS FOR DELIVERING AIR-BORNE SUBSTANCES

This nonprovisional application claims the benefit of prior Provisional Application No. 60/035,427 Jan. 22, 1999.

FIELD OF THE INVENTION

The present invention is directed to apparatus for delivering air-borne substances and, more particularly, to apparatus which deliver such substances from pulsatile devices yet do so in a uniform (i.e., non-pulsatile) manner.

BACKGROUND OF THE INVENTION

Metered dose inhalers ("MDIs") have been the preferred method of delivery of drugs for treatment of asthma and other diseases of the respiratory tract for over twenty years. Human beings open their mouths voluntarily to inhale a therapeutic bolus, while animal models used in inhalation toxicology must be tested using continuous flow systems. FDA requirements and good laboratory practices (GLP) specify that a uniform concentration of the drug be maintained, although the output from conventional MDIs is pulsatile. Additionally, the Montreal Convention requires that existing MDI formulations be replaced by more environmentally benign formulations, using new propellant mixtures to replace chlorofluoro hydrocarbons. FDA regulations also require that each new formulation be tested as if it were a new drug, creating a major need for more efficient toxicity testing of MDI devices.

Recently, pharmaceutical companies have developed a large number of biologically active peptides, many of which can be produced in bulk using genetically modified bacteria or animals such as goats. Although many such peptides degrade rapidly when ingested, studies have shown that when they are delivered to the alveoli they cross the lung/blood barrier without major degradation. Thus, aerosol delivery to the deep lung is the method of choice for many promising new peptide pharmaceuticals, many of which must be tested by studies in at least two models prior to initiation of clinical trials.

When a new pharmaceutical is being produced in the laboratory, it remains very expensive, even if scale-up following satisfactory toxicity testing is expected to reduce the ultimate price to consumers. Due to this expense, whenever possible the quantity of pharmaceutical (or toxicant) to be tested should therefore be minimized.

Flow past, nose-only exposure chambers have been developed for drug testing, and these have increasingly replaced whole body exposure chambers for pharmaceutical work. The flow rate required (typically 30 liters per minute (LPM)) is an order of magnitude less than that for whole body chambers, reducing toxicant consumption ten-fold. Current MDI aerosol generators, however, are rather inefficient in aerosol delivery. Typical delivery values range from 10% to 20%. Thus, a further three or four fold reduction in toxicant consumption can be expected to be achieved if delivery efficiencies are increased to the 60–80% range typical of most aerosol delivery systems used in animal exposures. Even a two-fold improvement would be significant.

This is particularly true with MDIs. The plume from a MDI spreads out to about three inches in diameter, and larger particles within the plume have a trajectory of about one foot. Thus, problems are encountered due to particle loss by impaction unless an adequate trajectory is allowed. A further problem is that an MDI produces a sudden burst of aerosol, or pulsatile flow, whereas the nose-only exposure chambers which meet GLP and FDA regulations must have a steady or uniform aerosol concentration delivered to them.

Existing systems attempt to solve the problems of plume impaction and pulsatile output by firing the MDIs (singly or in groups of up to six at a time) into a chamber of diameter 18 inches or more. Such systems contain a mixing chamber wherein the MDI plume flows in a horizontal direction and the dilution air flows in a vertical direction. The cross-sectional area of such chambers is approximately 1500 sq. cm. Thus, a flow rate of 30 LPM (required for a nose—only chamber) represents a mean upward velocity of 20 cm/min, giving a three foot tall chamber a mean residence/mixing time of almost five minutes. Data demonstrate that this is ample to damp out the pulsatile effect of MDIs fired at five second intervals. The output from the system is very stable and is not discernibly pulsatile. No special effort is made to ensure thorough mixing of the dilution air (drawn upwards by the exhaust system) with the horizontal MDI plumes. The data suggest an elaborate mixing system is not needed for a system with long mean residence times.

A possible draw-back to this approach is that it couples a generator with a slow rise time ($t_{90}$) of over ten minutes to a chamber with small internal volume and rapid rise time (approximately one minute). In addition, although the upward velocity of less than a cm/sec should be adequate to support particles of up to ten microns, most practical working generators employ linear velocities much higher than this to overcome the effects of turbulence in the mixing chamber. A review of available data on the efficiency of delivery of the existing systems suggests analytical to nominal (A/N) ratios between 0.1 and 0.2. These calculations are estimates, based on firing rates of the MDIs, nominal output per firing, and a 30 LPM flow-rate.

Consequently, there remains a need in the art for aerosol delivery systems which employ relatively rapid flow rates without the need for complex control systems to minimize pulsatile flow. An aerosol generating apparatus utilizing a much smaller diameter and coaxial flow of diluent air and MDI propellant should have a significantly reduced $t_{90}$, and a greater efficiency of delivery.

OBJECTS OF THE INVENTION

It is one object of the present invention to provide systems which deliver aerosol materials from a plurality of pulsatile delivery devices.

It is another object of the invention to provide systems which deliver aerosol materials in a substantially uniform manner from a plurality of pulsatile delivery devices.

It is a further object to provide systems which deliver aerosol materials from pulsatile devices yet do not require involved systems for mixing air with the materials emitted by such devices.

It is yet another object to provide aerosol delivery systems having flow rates that closely match those employed in typical animal exposure chambers.

BRIEF DESCRIPTION OF THE INVENTION

These and other objects are satisfied by the present invention, which provides apparatus and methods for uniform delivery of air-borne materials from pulsatile delivery devices by passing air and the emissions from such devices in a coaxial manner through a suitable mixing chamber. In preferred embodiments, the apparatus of the invention comprise a chamber defining an axis of air flow, a plurality of pulsatile delivery devices, actuator means in communication with the devices for selective actuation thereof, and air flow means for introducing air at a first end of the chamber and for flowing that air substantially along said axis. In accordance with the invention, the pulsatile delivery devices are positioned at the first end of the chamber such that actuation of the devices emits an air-borne substance substantially along the axis of air flow.

The present invention further provides processes for delivering air-borne substances in a uniform manner. Preferred processes involve the use of an apparatus comprising a chamber defining an axis of air flow and a plurality of pulsatile delivery devices positioned at a first end of the chamber such that actuation of the devices emits an air-borne substance substantially along the axis. These processes comprise actuating at least one of the delivery devices and introducing air into the chamber at the first end thereof such that the air flows substantially along the axis.

BRIEF DESCRIPTION OF THE DRAWINGS

The numerous objects and advantages of the present invention may be better understood by those skilled in the art by reference to the accompanying non-scale figures, in which:

FIG. 3 is an isometric view of an alternative embodiment of the apparatus shown in FIG. 1.

FIG. 4 is an end view of the apparatus shown in FIG. 3.

FIG. 5 is a table of dosage concentration data gathered using an apparatus of the invention.

FIG. 6 is a table of mass median aerodynamic diameter (MMAD) and geometric standard deviation ($\sigma_g$) data for different concentration levels gathered using an apparatus of the invention

DETAILED DESCRIPTION OF THE INVENTION

Figure 1:
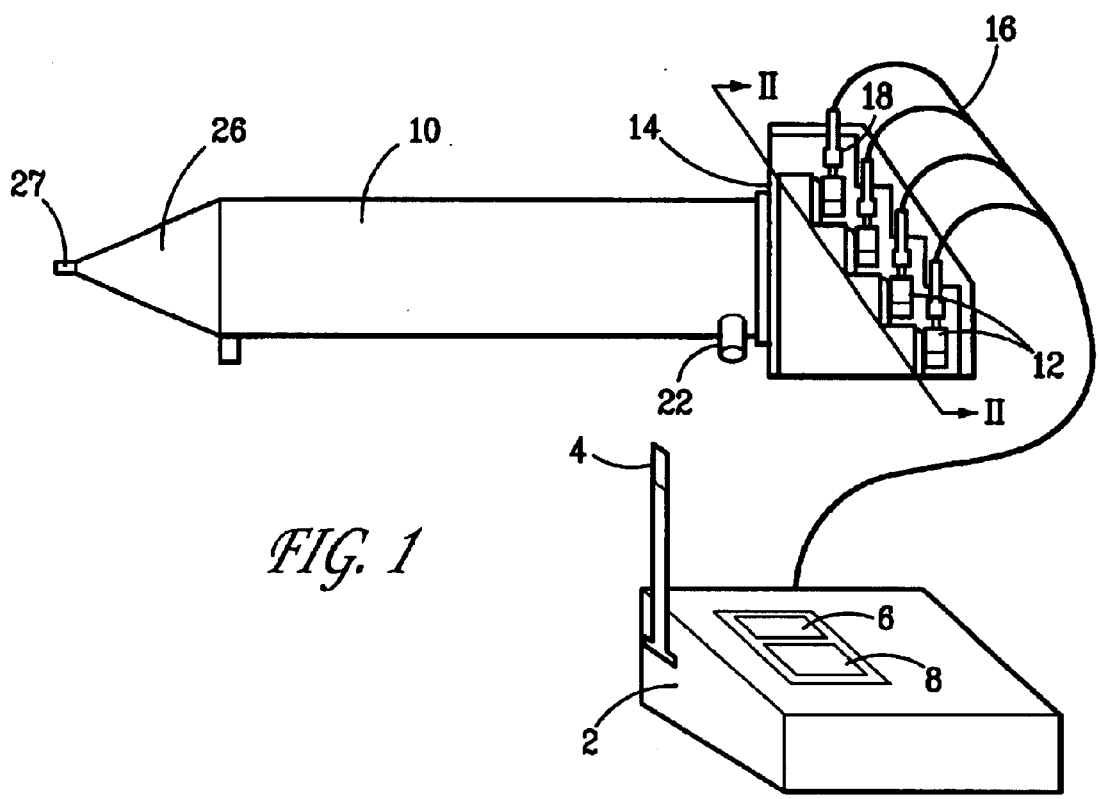
FIG. 1 is a plan view of an apparatus the invention.

The present invention provides apparatus and processes for delivering air-borne substances. An air-borne substance according to the invention is any material that can be transported in admixture with a stream of flowing air. Such substances can be in pure form or can themselves be mixtures of materials. They can be solids, liquids, and/or gases, although solid and liquid materials should be in a sufficiently finely divided state and/or of sufficiently low density that they remain in the air steam over a suitable distance of interest. Air-borne materials in the form of powdered solids or small droplets of liquids are preferred.

The apparatus of the invention include a chamber generally defining an axis of air flow. The chamber need not have any particular shape. Preferred shapes are those which present lateral cross-sections of relatively constant size along the chamber's length. The shape of such lateral cross-sections can be any closed-plane shape such as, for example, an ellipse (i.e., a circle or oval), a triangle, a tetrahedron, a hexagon, or a more complex polyhedron. Cylindrical chambers (i.e., those having circular cross-section) are preferred. The chamber also need not have any particular dimensions, although it should have a length that is about 3 to 20 times its inner diameter, preferably about 4 to 10 times its inner diameter, more preferably about 4 to 6 times its inner diameter. It has believed that the chamber should have a length of about 30 to 200 centimeters, preferably about 60 to 120 centimeters. The chamber can be constructed from virtually any material which has sufficient structural integrity to serve as a conduit for air. The chamber material should be inherently non-porous and inert to the air-borne substances employed, or should be a material which can be rendered non-porous and inert through a suitable pretreatment (e.g., coating) process. Numerous materials suitable for fabrication of the chamber are known in the art, with aluminum, stainless steel, and polycarbonate being preferred.

Chambers according to the invention include air flow means at a first of their two ends. The air flow means introduces air into the chamber and transports that air in a generally axial manner to the chamber's other end. Air flowing through the chamber (as well as any material borne thereby) should have a velocity which matches the designed flow rate of the animal exposure chambers with which an apparatus of the invention is employed. For commercially available exposure chambers, this generally will be about 0.5 to 20 centimeters per second, preferably about 1.0 centimeters per second, with a total air flow ranging from about 10 to 200 LPM, usually about 20–40 LPM. A wide variety of suitable air flow means are known to those skilled in the art. The air flow means in certain embodiments takes the form of one or more holes, perforations, or other types of apertures in fluid communication (e.g., through a tube, pipe, or hose) with a pump, fan, or other means, for supplying pressurized air.

Pulsatile delivery devices according to the invention are those which emit a quantity of air-borne material (i.e., a plume) only upon actuation. These devices generally comprise a nozzle, spout, or some other means for directed release of the air-borne material. The pulsatile devices preferably are in communication with a button, plunger, switch, or some other type of release mechanism. Common propellant-containing canisters and squirt bottles provide representative examples of pulsatile delivery devices. Preferred devices are the metered dose inhalers which are widely used in the pharmaceutical industry to deliver drugs for the treatment of asthma and other diseases.

Pulsatile delivery devices preferably are positioned in the apparatus of the present invention at same end of the chamber at which air is introduced and, moreover, are positioned such that actuation thereof emits an air-borne substance substantially along the chamber's axis of air flow. This is accomplished, for example, by pointing the devices' nozzles into the chamber.

The number of delivery devices employed is generally dependent upon their rate of release of the substance of interest, the air flow rate, and the cylinder's dimensions and, thus, is determined empirically. It has been found, for example, that up to about 16 metered dose inhalers should be used for with a cylindrical chamber having length on the order of about 90 centimeters and inner diameter on the order of about 20 centimeters with an air flow rate of about 0.75 centimeters per second. It is believed that up to about 32 delivery devices can be used, preferably up to about 16.

The delivery devices preferably are positioned in rows at one end of the chamber. These rows can, for example, be in a "stepped" configuration with respect to the chamber's inner diameter and axis of air flow, as shown in FIG. 1. It is particularly preferred that each of the devices within a row be contained in a single, removable cassette to facilitate removal of the devices when empty.

The pulsatile delivery devices should be in mechanical and/or electrical communication with suitable means for their actuation (i.e., release of air-borne material). Any actuator means known in the art can be used which is suitable for selective actuation of the delivery devices. Manual, automatic, and semi-automatic means for actuation can be employed, although some means of automation is preferred when more than about 4 devices are employed. One preferred means for actuation involves application of mechanical (e.g., pneumatic) pressure to the devices' release mechanisms using some suitable control means. Control means amenable to the practice of this invention include computing devices such microprocessors, microcontrollers, capacitors, switches, circuits, logic gates, or equivalent logic devices.

It is particularly preferred to partition the pulsatile delivery devices into groups which have an equal number of members and which are actuated simultaneously at fixed intervals. The respective groups, in turn, are actuated sequentially, also at fixed intervals. These intervals preferably range from about 2 to 180 seconds long. As will be recognized, the air-borne material emitted by the pulsatile delivery devices will, in accordance with the invention, have an average residence time in the chamber. This residence time should be at least 5 times greater than the fixed intervals between actuation of the groups and, more preferably, at least 10 times greater.

The delivery apparatus of the invention preferably are in fluid communication with at least one animal exposure chamber. To facilitate the transfer of air-borne materials to such chambers, the chamber preferably is equipped at its second end with a cone or some other type of reducing adapter of suitable dimensions. In preferred embodiments, the reducing adapter effects an approximately 2 to 40 fold diameter reduction with respect to the chamber's inner diameter, preferably 4 to 8 fold.

Figure 2:
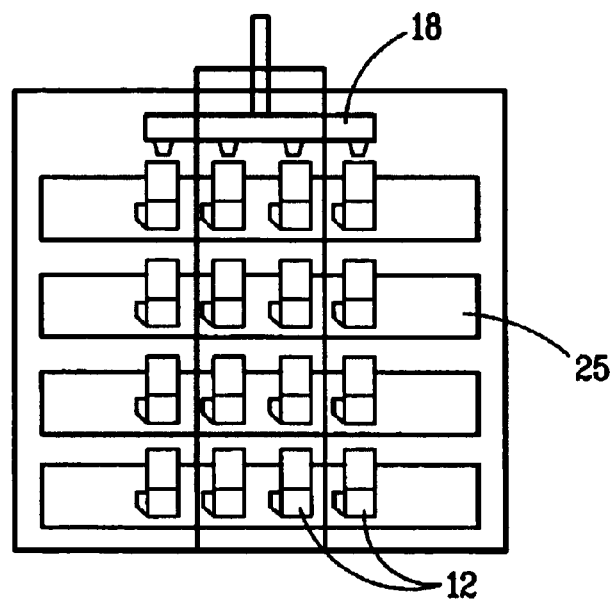
FIG. 2 is a cross-sectional view of the apparatus shown in FIG. 1, taken along line II—II.

One preferred apparatus according to the invention is shown in FIGS. 1 and 2. Control unit 2, consisting of a status indicator 4, display 6, and keypad 8, controls the flow of drug product into the plenum mixer generator chamber 10 by means of individual pulsatile delivery devices 12 having actuator means in the form of plunger bars 18 and compressed air lines and associated wiring 16. The devices (MDIs) are shown positioned on end-plate 14 in a stepped arrangement within cassettes 25 to maximize placement density. The delivered aerosol exits chamber 10 through exit tube 27, as shown.

In one variant of the device, filtered compressed air is fed to the four inlet ports 22, with the inlet flow controlled by needle valves and monitored by digital readout flow meters. In certain embodiments, filtered air from a class 100 exposure room is drawn in through the same inlet ports, with the exhaust system drawing air through both the exposure chamber and the mixing plenum. When the pressurized airway is supplied only to the inlet ports, any slight change in the performance of the exhaust system during exposures could result in the entire exposure system ceasing to be at the required negative pressure with respect to the room, and unacceptable exposure of personnel to the test article. This hazard can be avoided when the air supply to the inlet ports is drawn in by the exhaust system.

FIGS. 3 and 4 show an alternative design, in which chamber 10 and associated elements are mounted on planar base 28. This design includes o-ring equipped wheels 30 coupled with motor 32 to rotate the chamber, a rigid central ring 34 to restrain horizontal movement, a counterbalance 36, and a rotary coupling 38 and coupling bracket 40.

Such an apparatus preferably provides an unobstructed path from the MDI heads in the generator/diluter of at least 18 inches. This distance is sufficient both to allow evaporation of the propellant from the primary particles emitted by the MDI, and to avoid loss of test article by impaction of the primary particles, which are ejected from the MDI at speeds as great as 50 meters per second. The MDI plumes and the dilution air in this design both flow along the horizontal axis. The pulsatile flow is dampened (to 20% or less) by controlling the residence time in the mixing/dilution stage so that residence time exceeds the time between MDI bursts by at least five fold to ensure non-pulsatile aerosol delivery and to allow for evaporation of solvent.

Four rows of MDI cassettes 25, preferably fabricated from aluminum, are mounted on end plate 14, which also is fabricated from aluminum plate. Chamber 10 preferably is a seamless aluminum pipe, type 6061-T6, having 8.625 inch o.d. and 7.981 inch i.d.

To generate the concentration of aerosol required, up to sixteen MDI's are mounted in banks of four on stepped end plate 14. Each bank of four is activated by means of a pneumatic drive actuator. The pneumatic drives are controlled by a microprocessor, which fires the banks of MDIs sequentially. Each bank is activated up to six times a minute to achieve the concentration required. To minimize pulsatile aerosol generation, different banks of MDIs are fired at least every 90 seconds. Chamber 10 into which the MDIs fire preferably is three feet long to minimize plume impaction. The most frequent cause of system failure is jamming of an MDI valve. For this reason each set of four MDIs is mounted in a replaceable cassette. This design facilitates replacement of sets of MDIs when they are exhausted, or when an MDI fails.

Control unit 2 determines the intervals at which the MDIs in each row (or cassette) are activated or discharged. The control unit can be preset to supply air pressure, depressing plunger bar 18 above each cassette of MDI, at intervals ranging from 2 to 90 seconds. If the concentration data demonstrate that the activation interval chosen does not produce the targeted concentration, the firing interval is adjusted. The control unit is used to control the length of time for which pressure is applied (hold-down time) and to record the number of times each row (or cassette) has been discharged. Most MDIs are rated for less than 200 activations. The control unit preferably flashes (green) when a cassette has reached within six activations of its rated capacity; this changes to a red warning light if the cassette is not replaced, and the unit reset. The row which needs replacing is automatically skipped until it is replaced and the unit reset. The red warning light also displays if a cassette does not properly depress (jams). The control unit automatically skips this row until the cassette is replaced and the unit reset.

The apparatus as presently configured has been used for homogeneous solutions of pharmaceutical dissolved in ethanol and propellant (HCFC), which does not require inversion and mixing of the contents of the MDI prior to its discharge. Most MDI's are suspensions, and require inversions (thorough mixing) before discharge. The unit is designed to be symmetrical about its long axis, so that it can be mounted on rollers 30 and rotated (180°) about this axis. This inverts all the MDIs mounted on the end-plate. The number of inversions made prior to discharge is set in the electronic control unit. The number is chosen to equal to those planned in clinical trials.

Dilution sheath/mixing air is introduced immediately down-stream of end-plate 14, using an adaptation of a porous plug diluter. Dilution air is drawn in through four symmetrically placed ports 44 having 0.5 inch (i.d.) Inside chamber 10 and immediately opposite each port is an aluminum spreader plate. Dilution air entering through port 44 strikes the spreader plate 46 and is forced through a pair of fine wire gauze sheets 48 (100 mesh market grade stainless steel wire cloth, Newark Wire Cloth Company, Newark, N.J.) to spread the air uniformly. Tests on a plexiglass mockup demonstrate that four entry ports and spreader plates are essential to a uniform radial distribution of sheathing dilution air in the generator/mixer tube.

A flow rate of 15, 20 or 30 liters per minute (LPM) is used. With a chamber diameter of eight inches, this provides a linear velocity of 0.75 cm/sec at 15 LPM, adequate to efficiently transport aerosol out of the dilution/mixing chamber, while providing sufficient mixing/residence time (approximately one minute) to damp out the pulsatile nature of the primary aerosol. The $t_{90}$ for the system is five minutes at 30 LPM or 10 minutes at 15 LPM, which is compatible with that of the nose-only exposure chambers (seven minutes).

Chamber 10 ends in a conical reducing adapter 26 of a 45 degree angle. One inch brass tubing can be used to lead to the brass inlet nozzle of the anodized aluminum nose-only flow-past exposure chamber, such as those available from Intox, Albuquerque, N.Mex. (not shown). The exposure chamber design ensures that rebreathing, with consequent variability in animal exposure, is minimized. The nose-only exposure tubes typically are made of polycarbonate, with anodized aluminum nose-cones, and Cannon butt-plates. The exposure tube design is a marked improvement over other commercial designs, as it enables animals to exit from the front of the tube at exposure termination, reducing stress on the animals and excessive animal handling.

The apparatus of the invention has been used successfully for both rat nose-only and rabbit head-only exposures. Other modes of operation with other animals, such as mouth only dog exposures, are contemplated as well. Animals are brought into the inhalation facility, and loaded into nose-only exposure tubes. The last animal loaded for each chamber has a rectal probe inserted to monitor body temperature. As soon as animal loading is complete, the microprocessor controlling the pneumatic activators of the cassettes is switched on, and the exposure commenced. Cassettes of MDIs are replaced at intervals determined during pre-exposure trial runs. At the end of the exposure period, animals remain in the tubes for an additional ten-minute period, so that aerosol has cleared from the generator/mixer and exposure chamber before animal removal commences. Each animal is examined as it is removed and returned to its home cage. Filters are then removed from the sampling ports, weighed, and analyzed. Room temperature, relative humidity, flow rate and pressure are recorded throughout exposure. Room temperature and relative humidity were recorded throughout exposure.

Additional objects, advantages, and novel features of this invention will become apparent to those skilled in the art upon examination of the following examples thereof, which are not intended to be limiting.

EXAMPLE 1

Anodized aluminum cones such as typically used for animal exposure tubes, were attached to the chamber depicted in FIG. 3 for aerosol sampling. The cones were positioned so that the geometry is similar to that in the exposure tubes, but the point of sampling is approximately 0.2 inches closer to the aerosol manifold than the animal's nose. The anodized cones differed from those holding animal exposure tubes in that they have been drilled to accommodate a standard 0.25 inch inner diameter, 0.5 inch outer diameter quick connect brass sampling coupling, with grooves for two VITON O-rings (Rocket Seals Corporation, Denver, Colo.). The MDIs were actuated at 5 to 60 second intervals, with pressure supplied for one second. Air was introduced into the chamber at a pressure of 10 psi in one variant, and atmospheric pressure in another, to achieve a flow rate of 10–40 LPM. Impactor and filter samples were taken from the nose-only exposure chamber. A light scattering monitor can be employed to give rapid qualitative monitoring of exposure levels, so that any sudden change in aerosol concentration is noted rapidly.

Results are shown in FIG. 5.

EXAMPLE 2

Particle size distribution was measured using an INTOX eight-stage cascade impactor. Samples were taken during a prestudy testing period to determine particle size distribution. Size distributions were reported in terms of the Geometric Standard Deviation (GSD ($\sigma_g$)) and the Mass Median Aerodynamic Diameter (MMAD, in $\mu$m), as determined by the cascade impactor. This analysis was based on an algorithm describing test article aerosols which are distributed normally with respect to the logarithm of aerodynamic equivalent diameter (the diameter of a unit density sphere with the same settling velocity as the particle). Gravimetric and HPLC analyses of cascade impactor filters were both performed, but the results based on the HPLC analysis of test article on the filters data were considered the definitive measure of particle size.

Results are shown in FIG. 6.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. An apparatus for delivering air-borne substances, comprising:

a structure comprising a chamber, wherein said chamber defines an axis of air flow;

an air flow device at a first end of said chamber for introducing air and flowing air substantially along said axis;

a plurality of pulsatile delivery devices positioned at said first end of said chamber such that actuation of said devices emits an air-borne substance substantially along said axis; and an actuator in communication with said delivery devices for selective actuation thereof;

wherein:

said pulsatile delivery devices are positioned within a plurality of cassettes; or said axis of air flow is substantially perpendicular to the forces of gravity and said apparatus can be rotated about said axis of air flow.

2. The apparatus of claim 1 wherein said chamber is cylindrical.

3. The apparatus of claim 1 wherein said chamber has a length that is about 3 to 20 times its inner diameter.

4. The apparatus of claim 1 wherein said chamber has a length that is about 4 to 10 times its inner diameter.

5. The apparatus of claim 1 wherein said chamber has a length that is about 4 to 6 times its inner diameter.

6. The apparatus of claim 1 wherein said chamber has a length of about 30 to 200 centimeters.

7. The apparatus of claim 1 wherein said chamber has a length of about 60 to 120 centimeters.

8. The apparatus of claim 1 comprising up to about 32 pulsatile delivery devices.

9. The apparatus of claim 1 comprising about 16 pulsatile delivery devices.

10. The apparatus of claim 1 wherein said pulsatile delivery devices are positioned in rows at said first end of said chamber.

11. The apparatus of claim 1 wherein said pulsatile delivery devices are positioned within a plurality of cassettes.

12. The apparatus of claim 1 wherein said air flow device comprises at least one port at said first end of said chamber.

13. The apparatus of claim 1 wherein said port is in communication with a source of air at a pressure that is equal to or greater than atmospheric pressure.

14. The apparatus of claim 1 further comprising a reducing adapter in fluid communication with said chamber at a second end thereof.

15. The apparatus of claim 14 wherein said reducing adapter is conical.

16. The apparatus of claim 14 wherein said chamber has an inner diameter and said reducing adapter effects approximately 2 to 40 fold reduction in the cross-sectional area of air flow with respect the to said chamber inner diameter.

17. The apparatus of claim 1 mounted upon a substantially planar base.

18. The apparatus of claim 17 which can be rotated about said axis of air flow.

19. A process for delivering air-borne substances, comprising the steps of:

providing an apparatus comprising:

a cylindrical chamber defining an axis of air flow; and a plurality of pulsatile delivery devices positioned at said first end of said chamber such that actuation of said devices emits an air-borne substance substantially along said axis;

introducing air into said chamber at a first end thereof such that said air flows substantially along said axis; and actuating at least one of said delivery devices;

wherein:

said delivery devices are actuated at fixed intervals; or a plurality of said delivery devices are actuated simultaneously, thereby defining a group and at least two groups are actuated sequentially with respect to each other.

20. The process of claim 19 wherein said air flows with a velocity of about 0.5 to 5 centimeters per second with a total air flow form about 10 to 200 LPM.

21. The process of claim 19 wherein said delivery devices are actuated at fixed intervals.

22. The process of claim 19 wherein said delivery devices are actuated simultaneously.

23. The process of claim 19 wherein a plurality of said delivery devices are actuated simultaneously, thereby defining a group.

24. The process of claim 23 wherein there are a plurality of said groups and said groups are actuated sequentially.

25. The process of claim 24 wherein said groups are actuated at fixed intervals.

26. The process of claim 25 wherein said intervals are about 2 to 180 seconds long.

27. The process of claim 25 wherein said air-borne substance has an average residence time in said chamber which is at least 5 times greater than said intervals.

* * * * *